United States Patent [19]

Grote et al.

[11] 4,451,670

[45] May 29, 1984

[54] PREPARATION OF ISOBUTYRYL FLUORIDE

[75] Inventors: Dace Grote; Robert A. Grimm; Richard V. Norton, all of Columbus, Ohio

[73] Assignee: Ashland Oil, Inc., Ashland, Ky.

[21] Appl. No.: 438,443

[22] Filed: Nov. 2, 1982

[51] Int. Cl.$^3$ .................. C07C 51/10; C07C 51/04
[52] U.S. Cl. .................. 562/606; 260/544 A; 562/520
[58] Field of Search .................. 260/544 A; 562/520, 562/606

[56] References Cited

U.S. PATENT DOCUMENTS

| | | | |
|---|---|---|---|
| 2,580,070 | 12/1951 | Brooks et al. | 260/544 A |
| 3,354,198 | 11/1967 | Friedman et al. | 260/544 A |
| 3,414,612 | 12/1968 | Tan et al. | 260/544 A |
| 4,303,594 | 12/1981 | Norton et al. | 260/544 A |

*Primary Examiner*—Natalie Trousof
*Assistant Examiner*—L. Hendriksen
*Attorney, Agent, or Firm*—John F. Jones

[57] ABSTRACT

A process for the production of isobutyryl fluoride by reacting isopropyl fluoride and carbon monoxide in the presence of anhydrous hydrofluoric acid is described.

3 Claims, No Drawings

PREPARATION OF ISOBUTYRYL FLUORIDE

This invention relates to the production of isobutyryl fluoride by the carbonylation of isopropyl fluoride and more particularly pertains to the process for carbonylation of isopropyl fluoride to isobutyryl fluoride in the presence of anhydrous hydrogen fluoride at a temperature in the range of from 0° to 80° C. and at a pressure in the range of from 150 to 700 psi.

Isopropyl fluoride is a well-known material useful for may purposes well-known to those skilled in the art. Isopropyl fluoride can be prepared from propylene and hydrogen fluoride as shown in U.S. Pat. No. 2,917,559, for instance.

The preparation of certain acyl fluorides by reaction of acyl chlorides with certain inorganic fluorides is known. Another method for preparing certain acyl fluorides is by reacting certain secondary organic chlorides or bromides with carbon monoxide in the presence of boron trifluoride as catalyst, and hydrogen fluoride as shown in U.S. Pat. No. 2,570,793. Tertiary chlorides and bromides have been reacted with carbon monoxide in the presence of a catalyst like boron trifluoride and hydrogen fluoride to give acyl fluorides as disclosed in U.S. Pat. No. 2,580,070.

U.S. Pat. No. 3,414,612 describes a method for converting certain chloro- or bromo-substituted hydrocarbons such as tertiary butyl chloride, tertiary butyl bromide, 1,2-dichloro-2-methyl propane or 1,2-dibromo-2-methyl propane to the corresponding pivalyl fluoride by reaction of these materials with carbon monoxide using anhydrous hydrogen fluoride as catalyst (and obviously as a reactant). The process described in this patent is preferably carried out at a pressure of at least 750 psi and best results (90+% yields) occur at pressures in excess of 1500 psi.

Kanbara et al, *Bull. Jap. Pet. Inst.*, 11, 48–53 (1969) describe the reaction of ethyl fluoride with carbon monoxide and anhydrous hydrogen fluoride at high pressure followed by water treatment to yield propionic acid. Kanbara et al state at page 51 "in the autoclave the real product must be propionyl fluoride, but this hydrolyzes readily to give propionic acid when it is poured into water." The Kanbara et al process is carried out at a temperature of 100° C. or greater and at pressures of 2520 psi or greater. The higher temperatures and pressures give significant improvement in yields in the Kanbara et al process.

It is an object of this invention to provide a process for the production of isobutyryl fluoride by the relatively mild reaction of isopropyl fluoride with carbon monoxide. Another object of this invention is the production of isobutyric acid and/or isobutyric acid esters by the reaction of isopropyl fluoride with carbon monoxide followed by treatment of the resulting isobutyryl fluoride with water and/or alcohols.

These and other objects are accomplished by reacting carbon monoxide with isopropyl fluoride in the presence of anhydrous hydrogen fluoride at temperatures in the range of from 0° to 80° C. and at pressures in the range of from 150 to 700 psi, to produce isobutyryl fluoride.

The amount of anhydrous hydrogen fluoride employed in our process can be expressed as mole per mole of the isopropyl fluoride, Mole ratios of from 4.5:1 to 40:1 can be employed with ratios of from 9:1 to 20:1 being preferred.

The carbonylation process of this invention can be carried out at temperatures in the range of from 0° to 80° C. with a range of from 20° to 80° C. being preferred. Reaction temperatures above 80° C. significantly diminish the yield of isobutyryl fluoride.

The amount of pressure which is employed in the process of the present invention may be varied from about 150 to 700 psi, but preferably kept in the range of from 400 to 600 psi.

Reaction times are generally in the order of 30 to 50 minutes but longer times can be used.

The major product of the reaction is isobutyryl fluoride in yields of 89% or better.

Any suitable method for the isolation of isobutyryl fluoride from the reaction mixture may be used in our process. Furthermore, our process can be operated either batchwise or continuously. For instance, the excess hydrogen fluoride and carbon monoxide in the reaction effluent can be recycled to the reaction. As has been indicated earlier, the isobutyryl fluoride product, which is quite reactive, can be readily converted by solvolysis to the corresponding isobutyric acid, esters or amides.

Our invention is further illustrated in the following examples.

EXAMPLE 1

The reaction was carried out in a 300 cc capacity Hasteloy C Magnedrive reactor. The reactor was charged with 92 g. of anhydrous hydrogen fluoride and was pressurized with carbon monoxide to about 500 p.s.i.g. Isopropyl fluoride (using nitrogen partial pressure to maintain liquidity) was pumped from another cylinder into the vapor space of the reactor over a period of 26 minutes while maintaining a pressure of carbon monoxide at 477–553 p.s.i.g. In about 33 minutes reaction time (including addition time) at a reaction temperature of 50° C. the pressure in the reactor became stabilized indicating substantially complete reaction. After another 26 minutes under these conditions the reactor contents were cooled, 39 g. of water (2.2 moles) were added to the reactor and the gaseous material was vented from the reactor bringing the contents to about atmospheric pressure. The liquid in the reactor was transferred and further diluted with water to a 10–15% HF/H$_2$O solution containing the hydrolyzed carbonylation products 400 g of sodium sulfate was added and the resulting mixture was treated with cyclohexane to extract isobutyric acid from the aqueous phase. GC analysis showed a 94% yield of isobutyric acid was obtained.

EXAMPLE 2

The apparatus and parts of the procedure described in Example 1 were used in this Example. The reactor was charged with 91 g. of anhydrous hydrogen fluoride and the reactor was then pressurized to about 500 p.s.i.g. with carbon monoxide at 50° C. to the reactor then was added 30.6 g., (0.49 moles) of isopropyl fluoride by pumping it as a liquid under nitrogen pressure through a 20 gauge needle (0.02" ID) positioned in an entry port located below the surface of the anhydrous hydrogen fluoride in the reactor. The total amount of isopropyl fluoride was pumped to the reactor which was maintained at 50° C. over a period of about 25 minutes. The pressure which was maintained within the reactor at from about 475–569 p.s.i.g. with carbon monoxide stabilized in about 33 minutes after the isopropyl fluoride was first introduced. The reaction mixture was worked up as described in Example 1 to give a yield of 93% of isobutyric acid.

We claim:

1. The process for preparing isobutyryl fluoride consisting of contacting isopropyl fluoride, carbon monoxide and anhydrous hydrogen fluoride at a temperature in the range of from 0° C. to 80° C. and at a pressure in the range of from 150 to 700 psi.

2. The process of claim 1 wherein the mole ratio of anhydrous hydrogen fluoride to isopropyl fluoride is from 4.5:1 to 40:1.

3. The process of claim 2 wherein the isobutyryl fluoride is hydrolyzed with water to produce isobutyric acid.

* * * * *